US010273491B2

(12) United States Patent
Lee et al.

(10) Patent No.: US 10,273,491 B2
(45) Date of Patent: Apr. 30, 2019

(54) PROMOTER AND USES THEREOF

(71) Applicant: CJ CHEILJEDANG CORPORATION, Seoul (KR)

(72) Inventors: Seung Bin Lee, Seoul (KR); Hyun Ae Bae, Incheon (KR); Ji Hye Lee, Anyang-si (KR); Young Lyeol Yang, Seoul (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 15/547,398

(22) PCT Filed: Jan. 15, 2016

(86) PCT No.: PCT/KR2016/000444
§ 371 (c)(1),
(2) Date: Jul. 28, 2017

(87) PCT Pub. No.: WO2016/122146
PCT Pub. Date: Aug. 4, 2016

(65) Prior Publication Data

US 2018/0066269 A1 Mar. 8, 2018

(30) Foreign Application Priority Data

Jan. 29, 2015 (KR) ........................ 10-2015-0014587

(51) Int. Cl.

| | |
|---|---|
| ***C07H 21/04*** | (2006.01) |
| ***C12N 1/20*** | (2006.01) |
| ***C12N 15/00*** | (2006.01) |
| ***C12P 21/04*** | (2006.01) |
| ***C12N 15/77*** | (2006.01) |
| ***C12N 15/113*** | (2010.01) |
| ***C12P 13/04*** | (2006.01) |
| ***C12P 13/08*** | (2006.01) |
| ***C12P 13/10*** | (2006.01) |
| ***C12N 15/70*** | (2006.01) |

(52) U.S. Cl.
CPC .......... *C12N 15/77* (2013.01); *C12N 15/1137* (2013.01); *C12N 15/70* (2013.01); *C12P 13/04* (2013.01); *C12P 13/08* (2013.01); *C12P 13/10* (2013.01)

(58) Field of Classification Search
None
See application file for complete search history.

(56) References Cited

U.S. PATENT DOCUMENTS

| | | | | |
|---|---|---|---|---|
| 5,593,781 A | | 1/1997 | Nass et al. | |
| 5,641,660 A | | 6/1997 | Sinskey et al. | |
| 7,662,943 B2 | | 2/2010 | Park et al. | |
| 8,034,602 B2 | | 10/2011 | Park et al. | |
| 8,465,962 B2 | | 6/2013 | Kim et al. | |
| 8,512,987 B2 | | 8/2013 | Nagai et al. | |
| 8,703,446 B2 | | 4/2014 | Kiryukhin et al. | |
| 9,068,188 B2 | * | 6/2015 | Yun ........................ | C07K 14/34 |
| 2010/0317067 A1 | | 12/2010 | Kim et al. | |
| 2014/0147889 A1 | * | 5/2014 | Yun ........................ | C12N 15/77 435/69.1 |

FOREIGN PATENT DOCUMENTS

| | | | |
|---|---|---|---|
| CN | 101698844 | | 4/2010 |
| CN | 103827304 | A | 5/2014 |
| KR | 100620092 | | 9/2006 |
| KR | 100791659 | | 1/2008 |
| KR | 1020090082702 | | 7/2009 |
| KR | 101117022 | | 3/2012 |
| KR | 1020140110134 | | 9/2014 |
| RU | 2431672 | C2 | 10/2011 |
| RU | 2501858 | C2 | 12/2013 |
| RU | 2515044 | C2 | 5/2014 |
| WO | 2010017230 | A2 | 2/2010 |
| WO | 2017167623 | A1 | 10/2017 |

OTHER PUBLICATIONS

Bernhard J. Eikmanns, "A family of Corynebacterium glutamicum/*Escherichia coli* shuttle vectors for cloning, controlled gene expression, and promoter probing", Gene, (1991), vol. 102, pp. 93-98.

Jae Eun Paik, et al., "Isolation of transcription initiation signals from Corynebacterium ammoniagenes and comparison of their gene expression levels in *C. ammoniagenes* and *Escherichia coli*", Biotechnology Letters, (2003), vol. 25, pp. 1311-1316.

Jong-Kwon Han, et al., "Molecular Cloning and Expression of s-(2-Aminoethyl)-L-Cysteine Resistant Aspartokinase Gene of Corynebacterium glutamicum", Biotechnology Letters, (1991), vol. 13, No. 10, pp. 721-726.

Joseph Sambrook, et al., "Molecular Cloning", Laboratory manuals, (2001), pp. 1-21.

Marion M. Bradford, "A Rapid and Sensitive Method for the Quantitation of Microgram Quantities of Protein Utilizing the Principle of Protein-Dye Binding", Analytical Biochemistry, (1976), vol. 72, pp. 248-254.

Miroslav Pátek, et al., "Corynebacterium glutamicum promoters: a practical approach", Microbial Biotechnology, (Mar. 2013), vol. 6, Issue 7, pp. 103-117.

Miroslav Patek, et al., "Promoters from Corynebacterium glutamicum: cloning, molecular analysis and search for a consensus motif", Microbiology, (1996), vol. 142, pp. 1297-1309.

Taiwan Office Action—TW Application No. 59.120.175.116—US dated Jul. 6, 2017.

Yim, Sung Sun et al., "Isolation of Fully Synthetic Promoters for High-Level Gene Expression in Corynebacterium glutamicum", Biotechnology and Bioengineering, (Nov. 2013), vol. 110, Issue 11, pp. 2959-2969.

(Continued)

*Primary Examiner* — Yong D Pak
(74) *Attorney, Agent, or Firm* — Cantor Colburn LLP

(57) ABSTRACT

Provided are a novel promoter and a method of producing a target product using the same.

8 Claims, No Drawings

Specification includes a Sequence Listing.

(56) References Cited

OTHER PUBLICATIONS

Pavla Vasicova et al., Analysis of the Corynebacterium glutamicum dapA Promoter, 1999, p. 6188-6191, vol. 181, No. 19, Journal of Bacteriology.
Han Min Woo et al., Recent progress in development of synthetic biology platforms and metabolic engineering of Corynebacterium glutamicum, 2014, p. 43-51, 180, Elsevier.
Tobias Busche et al., Identifizierung von Promotoren in Corynebacterium glutamicum, 2014, p. 284-287, vol. 20, Issue 3, Springer.
IPA Full examination report for application No. 2016212931 dated Jun. 21, 2018.
Extended European Search Report for Application No. 16743624.5 dated Jul. 17, 2018.
Russian Office Action for Application No. 2017128034/10 dated Apr. 20, 2018.
Russian Search Report for Application No. 2017128034/10(048375) filed on Jan. 15, 2016.

* cited by examiner

PROMOTER AND USES THEREOF

CROSS-REFERENCE TO RELATED APPLICATION

This application claims the benefit of Korean Patent Application No. 10-2015-0014587, filed on Jan. 29, 2015, in the Korean Intellectual Property Office, the disclosure of which is incorporated herein in its entirety by reference.

TECHNICAL FIELD

One or more exemplary embodiments relate to a novel promoter and a method of producing a target product using the same.

BACKGROUND ART

To produce target products, e.g., L-amino acids, organic acids, or nucleic acid materials, with high yield by using microorganisms, there is a need to selectively control the expression of genes related to a number of metabolic processes in the microorganisms. In particular, there is a need to enhance the expression of target genes involved in a biosynthetic pathway of the target products, and for example, a modification of an expression regulatory sequence may be performed. Such a modification of the expression regulatory sequence may include, for example, a substitution a native promoter for a strong promoter, a modification of a native promoter, or a modification of a Shine-Dalgarno (SD) sequence. The substitution a native promoter for a strong promoter has been used the most, and in this regard, it is considered essential to develop a useful promoter.

However, strong promoters known in the art are limited, and may be expressed only in a limited microorganism. In some cases, the strong promoters may fail to exhibit strong expression effects at various intensity levels as desired.

A tac promoter derived from *Escherichia coli* is widely known as a strong promoter in the art. In the case of the genus *Corynebacterium*, a new promoter has been developed by modification of a native promoter (see Gene, 102, 93-98, 1991; Microbiology, 142, 1297-1309, 1996). For example, it was reported that a promoter derived from *Corynebacterium ammoniagenesis* had about 10% higher activity than that of the tac promoter derived from *E. coli* (see Biotechnol. Lett. 25, 1311-1316, 2003). In addition, as a strong promoter derived from *Corynebacterium ammoniagenesis*, promoters of Pcj1 to Pcj7 with various intensity levels have been developed and had strong promoter activity that is at least 10 times as large as that of the tac promoter (see KR 10-0620092). In addition, a promoter derived from *Brevibacterium flavum* MJ-233 (FERM BP-1497) was reported to have a stronger activity than that of the tac promoter, but had a difficulty in its expression in a microorganism other than a microorganism belonging to the genus *Brevibacterium* (see U.S. Pat. No. 5,593,781).

In this regard, when the inventors of the present inventive concept explore a region including a promoter sequence that can have various intensity levels in a variety of different microorganisms, a novel promoter synthesized according to the present inventive concept is found to be expressed in a variety of different microorganisms and to exhibit much stronger expression effects than those of the existing promoters known in the art, thereby completing the present inventive concept.

DISCLOSURE

Technical Problem

One or more exemplary embodiments include, a novel promoter, an expression regulatory sequence comprising the novel promoter, a vector including the novel promoter, a host cell including the vector, and a method of producing a target product using the host cell.

Technical Solution

According to one or more exemplary embodiments, there is provided a promoter comprising a nucleotide sequence represented by SEQ ID NO: 1. In the present inventive concept, the promoter is named "an o2 promoter (hereinafter, referred to as "Po2")".

The term "promoter" as used herein refers to a DNA region to which an RNA polymerase is combined to allow initiation of transcription of a gene that is operatively linked to the promoter, and may be positioned at a 5'-end of an initiation site for transcription of an mRNA.

A polynucleotide having promoter activity as used herein may be modified to some extents according to recent studies of several techniques, such as a directed evolution technique or a site-directed mutagenesis technique. For example, a promoter having a homology of 70% or more, 80% or more, 90% or more, or 95% or more to the nucleotide sequence represented by SEQ ID NO: 1 is also included within the scope of the present inventive concept.

The term "homology" as used herein refers to the degree (represented in percentage) of sequence identity between polynucleotide sequences. In the present specification, a homology of a sequence identical to a given polynucleotide sequence or a sequence having similar activity with that of a given polynucleotide sequence is represented in terms of "% homology". For example, the homology of polynucleotide sequences may be determined by using standard software, e.g., BLAST 2.0, to calculate parameters such as score, identity, and similarity. Alternatively, the homology of polynucleotide sequences may be identified by comparing sequences according to a hybridization method performed under defined stringent conditions. The defined and appropriate conditions for the hybridization method may be determined in consideration of methods that are well known to one of person skilled in the art (see Infra in Sambrook et al., 1989).

According to one or more exemplary embodiments, there is provided an expression regulatory sequence, which controls expression of a target gene, comprising the nucleotide sequence represented by SEQ ID NO: 1.

The term "expression regulatory sequence" as used herein refers to a DNA sequence used for expression of a coding sequence that is operatively linked to the DNA sequence in a host organism. Such an expression regulatory sequence may include, a promoter required for initiating transcription, an operator sequence for regulating transcription, a sequence encoding a suitable mRNA ribosome binding site, and a sequence for regulating termination of transcription and translation. For example, an expression regulatory sequence suitable for prokaryotes may include a promoter, an operator sequence, and a ribosome binding site, but is not limited thereto. An expression regulatory sequence includes Po2 of the present inventive concept may constitute, if necessary, one of person skilled in the art may constitute an expression regulatory sequence as described above.

According to one or more exemplary embodiments, there is provided a vector including the expression regulatory sequence and a target gene operatively linked to the expression regulatory sequence.

The term "operatively linked" as used herein refers to a linking between an expression regulatory sequence which controls a target gene (e.g., a promoter) and other nucleotide sequences. In this regard, the expression regulatory sequence may be able to control transcription and/or translation of the other nucleotide sequences.

The term "vector" as used herein refers to a DNA product including base sequences of a polynucleotide to encode a target protein that is operatively linked to an appropriate expression regulatory sequence to express the target protein. In addition, a plurality of nucleotide sequences may be bonded to or recombined with the vector so that a DNA sequence of a selected gene with an appropriate 3'-untranslated sequence, and a promoter may be introduced into a cell. The vector may be used for transformation in an appropriate host cell, and then, may be replicated regardless of the genome of the host cell. Alternatively, the vector may be integrated into the genome of the host cell. In addition, the vector may include the promoter or a variant thereof and the target gene, and furthermore, may include a replication origin, a promoter regulatory site, a ribosome binding site, a transcription termination site, a selective marker, or a combination thereof.

The vector used in the present inventive concept is not particularly limited so long as it can be replicated in a host cell, and any vector available in the art may be used. Examples of the vector typically used in the art include a natural or recombinant plasmid vector, a cosmid vector, a viral vector, and a bacteriophage vector. Examples of the bacteriophage and cosmid vectors include pWE15, M13, λMBL3, λMBL4, λIXII, λASHII, λAPII, λt10, λt11, Charon4A, and Charon21A, and examples of the plasmid vectors include pBR-based, pUC-based, pBluescriptII-based, pGEM-based, pTZ-based, pCL-based, and pET-based vectors, but the vectors are not limited thereto.

The target gene refers to a gene encoding a product to be expression in an excess amount. For example, the target gene may be a gene involved in the production of a product selected from the group consisting of amino acids (e.g., L-amino acid), organic acids, and a combination thereof. In detail, the target gene may be a gene encoding an enzyme involved in biosynthesis of amino acids, a gene encoding an enzyme involved in biosynthesis of organic acids, or a gene encoding a protein involved in exporting a target product, but is not limited thereto.

According to one or more exemplary embodiments, there is provided a host cell including a vector, wherein the vector includes an expression regulatory sequence which controls a target gene and includes a promoter having a nucleotide sequence represented by SEQ ID NO: 1 and a target gene that is operatively linked to the expression regulatory sequence.

The host cell is not particularly limited so long as a microorganism used as the host cell is capable of introducing the vector including the expression regulatory sequence which controls a target gene and includes the promoter having the nucleotide sequence represented by SEQ ID NO: 1 and the target gene that is operatively linked to the expression regulatory sequence. The host cell may be both a prokaryotic cell and a eukaryotic cell, but in an exemplary embodiment, may be a prokaryotic cell. For example, the host cell may include a strain of a microorganism belonging to the genus *Escherichia*, the genus *Erwinia*, the genus *Serratia*, the genus *Providencia*, the genus *Corynebacterium*, and the genus *Brevibacterium*. For example, the host cell may be a strain of a microorganism belonging to the genus *Corynebacterium* or the genes *Escherichia*. For example, the host cell may be a strain of a microorganism belonging to *Escherichia coli, Corynebacterium glutamicum, Corynebacterium thermoaminogenes, Brevibacterium flavum*, or *Brevibacterium lactofermentum.*

The introduction of the vector may be performed by, as described in the art, selecting a suitable technique according to the host cell. The introduction of the vector may be performed by, for example, electroporation, heat-shock, calcium phosphate ($CaPO_4$) precipitation, calcium chloride ($CaCl_2$) precipitation, microinjection, polyethylene glycol (PEG), a DEAE-dextran method, a cationic liposome method, a lithium acetate-DMSO method, or a combination thereof, but is not limited thereto.

According to one or more exemplary embodiments, there is provided a method of producing a target product, the method including: culturing a host cell in a medium, wherein the host cell comprise a vector that includes an expression regulatory sequence comprising a promoter having a nucleotide sequence represented by SEQ ID NO: 1 and a target gene that is operatively linked to the expression regulatory sequence; and recovering the target product from the host cell or the medium including the cultured host cell.

The target product may be selected from the group consisting of amino acids (e.g., L-amino acid), organic acids, and a combination thereof. The term "amino acid" or "L-amino acid" as used herein generally refers to a basic unit of a protein constituting a living body, in which an amino acid group and a carboxyl group are linked to the same carbon atom. The amino acid may be selected from the group consisting of glycine, alanine, valine, leucine, isoleucine, threonine, serine, cysteine, cystine, methionine, aspartic acid, asparagine, glutamic acid, diiodotyrosine, lysine, arginine, histidine, phenylalanine, tyrosine, tryptophan, proline, oxyproline, and a combination thereof, but is not limited thereto. The term "organic acid" as used herein refers to an organic compound having acidity, and for example, may include an organic compound having a carboxyl group and a sulfonic group. The organic acid may include, for example, lactic acid, acetic acid, succinic acid, butyric acid, palmitic acid, oxalic acid, tartaric acid, propionic acid, hexenoic acid, capric acid, caprylic acid, valeric acid, or citric acid, but is not limited thereto.

The culture of the host cell may be performed according to typical methods known in the art. The medium used for the culturing of the host cell may include, as a source of sugar, sugar and carbohydrates, such as glucose, saccharose, lactose, fructose, maltose, starch, and cellulose; oils and fats, such as soybean oil, sunflower oil, castor oil, and coconut oil; fatty acids, such as palmitic acid, stearic acid, and linoleic acid; alcohols, such as glycerol and ethanol; and organic acids, such as acetic acid, individually or as a mixture, but is not limited thereto. The medium used for the culturing of the host cell may include, as a source of nitrogen, peptones, yeast extract, meat extract, malt extract, maize steep liquor, soybean meal, and urea, or inorganic compounds, such as ammonium sulfate, ammonium chloride, ammonium phosphate, ammonium carbonate, or ammonium nitrate, individually or as a mixture, but is not limited thereto. The medium used for the culturing of the host cell may include, as a source of phosphorus, potassium dihydrogen phosphate or dipotassium hydrogen phosphate, or its corresponding sodium-containing salts, but is not limited thereto. The medium used for the culturing of the host cell may include, salts of metals, such as magnesium sulfate or iron sulfate, which are needed for growth, but the salts of metals are not limited thereto. In addition, during the culturing of the host cell, essential growth substances, such as amino acids and vitamins, or suitable precursors may be added to the culture medium. Such materials may be added to the culture medium during the culturing of the host cell in an appropriate manner, and for example, may be added in a batch or continuous manner.

Furthermore, during the culturing of the host cell, compounds, such as ammonium hydroxide, potassium hydroxide, ammonia, phosphoric acid, and sulfuric acid, may be added to the culture medium in a suitable manner to regulate the pH of the culture medium. In addition, during the culturing of the host cell, an anti-forming agent, such as fatty acid polyglycol ester, may be used to prevent the production of foams. To maintain aerobic conditions of the culture medium, oxygen or oxygen-containing gas (e.g., air) may be introduced into the culture medium. Here, a temperature of the culture medium may be in a range of about 20° C. to about 45° C., for example, about 25° C. to about 40° C. In addition, the culturing of the host cell may be continued until a desired amount of a target product is achieved, and in this regard, the culturing of the host cell may be continues for about 10 hours to about 160 hours.

The recovering of the target product from the host cell or the culture medium including the cultured host cell may be performed (i.e., separated or recovered) through an appropriate reaction known in the art. For example, an appropriate reaction may be made according to a treatment using protein precipitants (i.e., a salting out method), centrifugation, extract, sonication, ultrafiltration, dialysis, various chromatography techniques, such as molecular sieve chromatography (i.e., gel filtration), adsorption chromatography, ion-exchange chromatography, affinity chromatography, and a combination thereof, but is not limited thereto. In this regard, the produced target product may be collected, recovered, or separated from the host cell or the medium including the cultured host cell.

MODE FOR INVENTION

Hereinafter, the present inventive concept will be described in further detail with reference to the following examples. However, these examples are for illustrative purpose only and are not intended to limit the scope of the present inventive concept.

Example 1: Preparation of a Recombinant Vector Comprising a Novel Promoter and a Transformed Strain Using the Same (1) Preparation of a Recombinant Vector Comprising Po2 and a Transformed Strain Using the Same In terms of synthesizing a promoter that induces expression of a target gene, sequences of various promoters derived from a microorganism belonging to the genus *Corynebacterium* and a microorganism belonging to the genus *Escherichia* were analyzed, thereby synthesizing a promoter having a nucleotide sequence of SEQ ID NO: 1. The synthesized promoter was referred to as an o2 promoter (hereinafter, named "Po2"). To measure a Po2 activity for inducing a target gene expression, the Po2 was operatively linked to an open reading frame (ORF) of a GFP gene so that a recombinant vector was prepared. Then, each of strains of Corynebacteria and *E. coli* was transformed with the recombinant vector, thereby preparing each of the transformed strains of Corynebacteria and *E. coli.*

In addition, to prepare a strain having an enhanced ability of producing L-amino acids, e.g., L-arginine, or branched amino acids, such as L-valine, as an example of a target product, the Po2 was used to enhance the expression of biosynthetic gene for arginine or valine.

(1.1) Preparation of a Vector pECCG117-Po2-gfp and a Transformed Strain Using the Same (1.1.1) Preparation of a Vector PCR was performed by using the synthesized Po2 as a template and a primer set of SEQ ID NO: 2 and SEQ ID NO: 3 including Kpn I/EcoR V restriction sites. The PCR was performed according to cycles of denaturation at a temperature of 94° C. for 5 minutes, denaturation at a temperature of 94° C. for 30 seconds, annealing at a temperature of 60° C. for 30 seconds, and polymerization at a temperature of 72° C. for 30 seconds, wherein the cycles were performed 30 times. Afterwards, polymerization was performed again on the strains at a temperature of 72° C. for 7 minutes, thereby consequently obtaining Po2 having a length of about 100 bp.

PCR was performed by using a pGFPuv vector (manufactured by Clontech, USA) as a template and a primer set of SEQ ID NO: 4 and SEQ ID NO: 5 including PstI/EcoR V restriction sites. PCR was performed according to cycles of denaturation at a temperature of 94° C. for 5 minutes, denaturation at a temperature of 94° C. for 30 seconds, annealing at a temperature of 55° C. for 30 seconds, and polymerization at a temperature of 72° C. for 1 minute, wherein the cycles were performed 30 times. Afterwards, polymerization was performed again at a temperature of 72° C. for 7 minutes, thereby consequently obtaining SEQ ID NO: 6 including the ORF of the GFP gene.

The Po2 was treated with restriction enzymes PstI and EcoR V and the ORF of the GFP gene was treated with restriction enzymes Kpn I and EcoR V, at PstI and Kpn I sites of a shuttle vector pECCG117 (see Biotechnology letters vol 13, No. 10, p. 721-726 (1991)) that can be expressed in *E. coli* and Corynebacteria. Then, the treated Po2 and ORF of the GFP gene were operatively linked to each other by using a DNA conjugating enzyme, thereby manufacturing a recombinant vector in which the Po2 and the GFP gene were linked to each other. Here, the recombinant vector was named pECCG117-Po2-gfp.

(1.1.2) Preparation of a Transformed Strain Using the Vector

*Corynebacterium glutamicum* ATCC13032 was transformed with each of a vector pECCG117 and the recombinant vector pECCG117-Po2-gfp by an electric pulse method, and then, transformed strains were obtained from a selective medium containing 25 mg/L of kanamycin. The obtained strains that were transformed with the vector pECCG117 and the recombinant vector pECCG117-Po2-gfp were each named ATCC13032/pECCG117 and ATCC13032/pECCG117-Po2-gfp.

In addition, *E. coli* DH5α was transformed with the recombinant vector pECCG117-Po2-gfp by a heat shock method, and then, transformed strains were obtained from a Luria-Bertani (LB) agar medium containing 25 mg/L of kanamycin. The obtained strains were named DH5α/pECCG117-Po2-gfp and assigned as a deposit designation "CA01-2290". CA01-2290 was deposited at the Korean Culture Center of Microorganisms (KCCM) on Oct. 23, 2014, under the accession number of KCCM11591P, in accordance with the terms of the Budapest Treaty on the International Recognition of the Deposit of Microorganisms for the Purposes of Patent Procedure.

(1.2) Preparation of a Vector pECCG117-Po2-argJ and a Transformed Strain Using the Same (1.2.1) Preparation of a Vector In terms of synthesizing a vector in which a main biosynthetic gene, e.g., an argJ gene (Ncgl1341, SEQ ID NO: 7) encoding bifunctional ornithine acetyltransferase/N-acetylglutamate synthase, for enhanced production of arginine is expressed by the Po2, the recombinant vector pECCG117-Po2-gfp was used to prepare a vector pECCG117-Po2-argJ.

In detail, PCR was performed on a strain by using chromosomes of *Corynebacterium glutamicum* ATCC13869 as a template and a primer set of SEQ ID NO: 8 and SEQ ID NO: 9, thereby ensuring DNA fragments including the argJ genes. The PCR was performed according to cycles of denaturation at a temperature of 94° C. for 1 minute, annealing at a temperature of 58° C. for 30 seconds, and polymerization at a temperature of 72° C. for 2 minutes by using a Pfu polymerase, wherein the cycles were performed 30 times. Consequently, a fragment having a length of about 1,201 bp and including EcoRV and 3' PstI restriction enzyme sites on a 5' end was amplified. The amplified fragments generated by the PCR were purified, mixed with the vector pECCG117-Po2-gfp to which EcoRV and PstI restriction enzymes were treated, and then, joined together using the In-fusion Cloning Kit, thereby preparing a recombinant vector, which was named pECCG117-Po2-argJ.

(1.2.2) Preparation of a Transformed Strain Using the Vector

*Corynebacterium glutamicum* KCCM10741P, which is an arginine producing strain, was transformed with the recombinant vector pECCG117-Po2-argJ by an electric pulse method (see KR 10-0791659), and then, transformed strains were obtained from a selective medium containing 25 mg/L of kanamycin. The obtained strain was named KCCM10741P/pECCG117-Po2-argJ.

(1.3) Preparation of a Vector pECCG117-Po2-ilvE and a Transformed Strain Using the Same (1.3.1) Preparation of a Vector In terms of synthesizing a vector in which a main biosynthetic gene, e.g., an ilvE gene (Ncgl2123, SEQ ID NO: 10) encoding a branched-chain amino acid aminotransferase, for enhanced production of valine is expressed by the Po2, the recombinant vector pECCG117-Po2-gfp was used to prepare a vector pECCG117-Po2-ilvE.

In detail, PCR was performed on a strain by using chromosomes of *Corynebacterium glutamicum* ATCC14067 as a template and a primer set of SEQ ID NO: 11 and SEQ ID NO: 12, thereby ensuring DNA fragments including the ilvE genes. The PCR performed according to cycles of denaturation at a temperature of 94° C. for 1 minute, annealing at a temperature of 58° C. for 30 seconds, and polymerization at a temperature of 72° C. for 2 minutes by using a Pfu polymerase, wherein the cycles were performed 30 times. Consequently, a fragment having a length of about 1,201 bp and including EcoRV and 3' PstI restriction enzyme sites on a 5' end was amplified. The amplified fragments generated by the PCR were purified, mixed with the vector pECCG117-Po2-gfp to which EcoRV and PstI restriction enzymes were treated, and then, joined together using the In-fusion Cloning Kit, thereby preparing a recombinant vector, which was named pECCG117-Po2-ilvE.

(1.3.2) Preparation of a Transformed Strain Using the Vector

*Corynebacterium glutamicum* KCCM111201P, which is a valine producing strain, was transformed with the recombinant vector pECCG117-Po2-ilvE by an electric pulse method (see KR 10-1117022), and then, transformed strains were obtained from a selective medium containing 25 mg/L of kanamycin. The obtained strains were named KCCM11201P/pECCG117-Po2-ilvE.

Comparative Example 1: Preparation of a Recombinant Vector Including a Control Promoter and a Transformed Strain Using the Vector To measure a Po2 activity for inducing a target gene expression, the GFP gene was used to operatively link a known strong promoter (e.g., Ptrc, Pcj1, Pcj4, or Pcj7 (see KR 10-0620092)) or a wild-type promoter (e.g., aceEP (WT)) to the ORF of the GFP gene to prepare a recombinant vector. Then, each of strains of Corynebacteria and *E. coli* was transformed with the recombinant vector, thereby preparing each of the transformed strains of Corynebacteria and *E. coli*.

In addition, to evaluate the transformed strains including a main biosynthetic gene using the Po2 for enhanced production of a target gene, a transformed strain including a main biosynthetic gene for enhanced production of arginine or a transformed strain including a main biosynthetic gene for enhanced production of valine were each prepared.

(1) Preparation of a gfp Expression Vector Having a Different Promoter from the Po2 in Terms of Activity Comparison with the Po2 and a Transformed Strain of *Corynebacterium glutamicum*

Base sequences of aceEP(WT) were ensured based on the U.S. National Institute of Health (NIH Genbank), and PCR was performed thereon by using chromosomes of wild-type *Corynebacterium glutamicum* ATCC13032 as a template and a primer set of SEQ ID NO: 13 and SEQ ID NO: 14 including Kpn I/EcoR V restriction sites. The PCR was performed in the same manner as in (1.1) of Example 1, thereby preparing a recombinant vector named pECCG117-aceEP(WT)-gfp.

Strains of *Corynebacterium glutamicum* were transformed with each of the prepared vector pECCG117-aceEP (WT)-gfp and vectors pECCG117-Pcj1-gfp, pECCG117-Pcj4-gfp, and pECCG117-Pcj7-gfp (see KR 10-0620092), in the same manner as in (1.1) of Example 1, thereby preparing transformed strains that were each named ATCC13032/pECCG117-aceEP(WT)-gfp, ATCC13032/pECCG117-Pcj1-gfp, ATCC13032/pECCG117-Pcj4-gfp, and ATCC13032/pECCG117-Pcj7-gfp.

(2) Preparation of a gfp Expression Vector Having a Different Promoter from the Po2 in Terms of Activity Comparison with the Po2 and a Transformed Strain of *E. coli*

Base sequences of Ptrc were ensured based on the U.S. National Institute of Health (NIH Genbank), and PCR was performed thereon by using pTrc99A (NCBI GenBank, M22744) as a template and a primer set of SEQ ID NO: 15 and SEQ ID NO: 16 including Kpn/EcoR restriction sites. The PCR was performed in the same manner as in (1.1) of Example 1, thereby preparing a recombinant vector named pECCG117-Ptrc-gfp.

Strains of *E. coli* were each of the prepared vector pECCG117-Ptrc-gfp and vectors pECCG117-Pcj1-gfp and pECCG117-Pcj4-gfp, in the same manner as in (1.1) of Example 1, thereby preparing transformed strains that were each named DH5α/pECCG117-Ptrc-gfp, DH5α/pECCG117-Pcj1-gfp, and DH5α/pECCG117-Pcj4-gfp.

(3) Preparation of a Transformed Strain Having a Different Promoter from the Po2 in Terms of a Target Product Producibility Comparison with the Po2

(3.1) Preparation of a Transformed Strain of *Corynebacterium glutamicum*, the Transformed Strain Having Arginine Producibility The vector pECCG117-Pcj7-gfp was used to prepare a vector named pECCG117-Pcj7-argJ in the same manner as in (1.2.1) of Example 1, except that PCR was performed by using a primer set of SEQ ID NO: 9 and SEQ ID NO: 17.

Then, a transformed strain was prepared by using the vector pECCG117-Pcj7-argJ in the same manner as in (1.2.2) of Example 1, and was named KCCM10741P/pECCG117-Pcj7-argJ.

(3.2) Preparation of a Transformed Strain of *Corynebacterium glutamicum*, the Transformed Strain Having Valine Producibility The vector pECCG117-Pcj7-gfp vector was used to prepare a vector named pECCG117-Pcj7-ilvE in the same manner as in (1.3.1) of Example 1, except that PCR was performed by using a primer set of SEQ ID NO: 12 and SEQ ID NO: 18.

Then, a transformed strain was prepared by using the vector pECCG117-Pcj7-ilvE in the same manner as in (1.3.2) of Example 1, and was named KCCM11201P/pECCG117-Pcj7-ilvE.

Example 2: Confirmation of a Po2 Activity for Inducing a Target Gene Expression (1) Confirmation of a Po2 Activity for Inducing a Target Gene Expression in *Corynebacterium glutamicum*

To measure a Po2 activity for inducing a target gene expression in the transformed strains of *Corynebacterium glutamicum*, the measurement of green fluorescence protein (GFP) activity of the transformed strain named ATCC13032/pECCG117-Po2-gfp of (1.1.2) of Example 1 was compared with the measurement of GFP activity of the transformed strains each named ATCC13032/pECCG117 of (1.1.2) of Example 1 and ATCC13032/pECCG117-aceEP(WT)-gfp, ATCC13032/pECCG117-Pcj1-gfp, ATCC13032/pECCG117-Pcj4-gfp, and ATCC13032/pECCG117-Pcj7-gfp of (1) of Comparative Example 1.

Each of the transformed strains of *Corynebacterium glutamicum* above was inoculated in a 250-ml corner bottle containing 25 ml of a seed medium by a volume ratio of 1:20, and then, shake-cultured (at a speed of about 200 rpm) at a temperature of 30° C. until the strains were grown in a culture metaphase phase (OD600=10.0). After completion of the culture, the cells were collected by centrifugation (at a speed of about 5,000 rpm for about 15 minutes). The collected cells were washed twice with a 0.1% Tris.HCl (pH 8.0) buffer solution, and then, suspended in the same buffer solution for a turbidity at 610 nm of about 160. The cells were disrupted for 6 minutes by using a bead beater after glass beads were added at 1.25 g/1.5 ml of the suspension. A supernatant containing a cell extract was collected by centrifugation (at a speed of about 15,000 rpm for about 20 minutes), and then, quantitatively measured in terms of a protein concentration therein according to the Bradford method (see Bradford, M. M 1976. Anal. Biochem. 72:248-254). Then, the same amount of the cell extract was irradiated with light at an excitation wavelength of 488 nm using the method of Laure Gory or the like, and light at an emission wavelength of 511 nm was measured by using the LS-50B spectrophotometer (Perkin-Elmer), thereby determining the expression of the GFP gene, The results of measuring GFP activity in each of the strains are shown in Table 1.

[Seed Medium]

20 g of glucose, 5 g of ammonium sulfate, 5 g of yeast extract, 1.5 g of urea, 4 g of KH2PO4, 8 g of K2HPO4, 0.5 g of MgSO47H2O, 150 μg of biotin, 1.5 mg of thiamine hydrochloride, 3 mg of calcium panthothenic acid, 3 mg of nicotinamide (based on 1 L of distilled water), and pH 7.2

TABLE 1

Fluorescence intensity in *Corynebacterium glutamicum*

| Strain | Fluorescence intensity |
|---|---|
| ATCC13032/pECCG117 | 0.0 |
| ATCC13032/pECCG117-Po2-gfp | 2339.5 |
| ATCC13032/pECCG117-aceEP(WT)-gfp | 170.7 |
| ATCC13032/pECCG117-Pcj1-gfp | 589.6 |
| ATCC13032/pECCG117-Pcj4-gfp | 920.5 |
| ATCC13032/pECCG117-Pcj7-gfp | 270.4 |

As shown in the results of Table 1, it was confirmed that the Po2 had a promoter activity in *Corynebacterium glutamicum*, and that the strain named ATCC13032/pECCG117-Po2-gfp exhibited fluorescence intensity that is at least 13 times as large as that of the wild-type ATCC13032/pECCG117-aceEP(WT)-gfp strain. In addition, it was confirmed that the strain named ATCC13032/pECCG117-Po2-gfp exhibited fluorescence intensity at a level that is much higher than that of the strains each named ATCC13032/pECCG117-Pcj1-gfp, ATCC13032/pECCG117-Pcj4-gfp, and ATCC13032/pECCG117-Pcj7-gfp using known strong promoters (e.g., Pcj1, Pcj4, and Pcj7). Consequently, it was confirmed that the Po2 served as a strong promoter to express a target gene.

(2) Confirmation of a Po2 Activity for Inducing a Target Gene Expression in *E. coli*

To measure a Po2 activity for inducing a target gene expression in the transformed strains of *E. coli*, measurement of GFP activity of the transformed strain named DH5α/pECCG117-Po2-gfp of (1.1.2) of Example 1 was compared with the measurement of GFP activity of the transformed strains each named DH5α/pECCG117-Ptrc-gfp, DH5α/pECCG117-Pcj1-gfp, and DH5α/pECCG117-Pcj4-gfp of (2) of Comparative Example 2.

Each of the transformed strains of *E. coli* above was inoculated in a 250-ml corner bottle containing 25 ml of a kanamycin-containing LB medium a volume ratio of 1:20, and then, shake-cultured (at a speed of about 200 rpm) at a temperature of until the strains were grown in a culture metaphase phase (OD600=3.0). After completion of the culture, the cells were collected by centrifugation (at a speed of about 5,000 rpm for about 15 minutes), washed twice with a 0.1% Tris.HCl (pH 8.0) buffer solution, suspended in the same buffer solution, disrupted by sonication, and then, subjected to centrifugation (at a speed of about 15,000 rpm for about 20 minutes) to obtain a supernatant containing a cell extract. The supernatant was quantitatively measured in terms of a protein concentration therein according to the Bradford method. Then, the same amount of the cell extract was irradiated with light at an excitation wavelength of 488 nm using the method of Laure Gory or the like, and light at an emission wavelength of 511 nm was measured by using the LS-50B spectrophotometer (Perkin-Elmer), thereby determining the expression of the GFP gene. The results of measuring GFP activity in each of the strains are shown in Table 2.

TABLE 2

| Fluorescence intensity in *E. coli* | |
|---|---|
| Strain | Fluorescence intensity |
| DH5α/pECCG117-Ptrc-gfp | 287.0 |
| DH5α/pECCG117-Po2-gfp | 248.9 |
| DH5α/pECCG117-Pcj1-gfp | 3041.9 |
| DH5α/pECCG117-Pcj4-gfp | 135.1 |

As shown in the results of Table 2, it was confirmed that the Po2 had a promoter activity in *E. coli*, and that the strain named DH5α/pECCG117-Po2-gfp exhibited the fluorescence intensity at a similar level with that of the strain named DH5α/pECCG117-Ptrc-gfp, which is a known as a strong promoter and higher than that of the DH5α/pECCG117-Pcj4-gfp strain. Consequently, it was confirmed that the Po2 served as a strong promoter to express a target gene in *E. coli*.

Example 3: Evaluation of Strains for Enhanced Target Product Producibility (1) Evaluation of Strains for Enhanced Production of Arginine In terms of evaluating factors influencing the production of arginine, when the main biosynthetic gene for arginine, i.e., the argJ gene, was expressed by using the Po2, the strain named KCCM10741P/pECCG117-Po2-argJ of (1.2.2) of Example 1, which was used as the strain for enhanced production of the argJ gene, was compared with the non-transformed strain named KCCM10741P (having no transformed arginine producibility) and the strain named KCCM10741P/pECCG117-Pcj7-argJ of (3.1) of Comparative Example 1 in terms of the arginine producibility.

1 loop of each of the transformed strains above was inoculated in a 250-ml corner bottle containing 25 ml of a production medium, and then, shake-cultured at a speed of about 200 rpm at a temperature of 30° C. for 48 hours. After completion of the culture, the production of L-arginine was measured by HPLC. The results of measuring the production of L-arginine are shown in Table 3.

[Production Medium]

glucose 6%, ammonium sulfate 3%, monopotassium phosphate 0.1%, magnesium sulfate heptahydrate 0.2%, corn steep liquor (CSL) 1.5%, NaCl 1%, yeast extract 0.5%, biotin 100 μg/L, and pH7.2

TABLE 3

| Production of arginine in KCCM10741P | | |
|---|---|---|
| Strain | OD | Concentration of arginine (g/L) |
| KCCM110741P | 89 | 3.1 |
| KCCM10741P/pECCG117-Pcj7-argJ | 85 | 4.6 |
| KCCM10741P/pECCG117-Po2-argJ | 82 | 5.7 |

As shown in the results of Table 3, it was confirmed that the Po2 resulted in improved production of arginine in *Corynebacterium glutamicum* in which the expression of the argJ gene was enhanced. In particular, the arginine production in *Corynebacterium glutamicum* was increased by about 84% compared to that in the control strain, and was increased by about 23% compared to that in the strain named KCCM10741P/pECCG117-Pcj7-argJ. Consequently, it was confirmed that the Po2 influenced the enhanced expression of the argJ gene.

(2) Evaluation of Strains for Enhanced Production of L-Valine

In terms of evaluating factors influencing the production of valine, when the main biosynthetic gene for valine, i.e., the ilE gene, was expressed by using the Po2, the strain named KCCM11201P/pECCG117-Po2-ilvE of (1.3.2) of Example 1, which was used as the strain for enhanced production of the ilvE gene, was compared with the non-transformed strain named KCCM11201P (having no transformed L-valine producibility) and the strain named KCCM11201P/pECCG117-Pcj7-ilvE of (3.2) of Comparative Example 1 in terms of L-valine producibility.

1 loop of each of the transformed strains above was inoculated in a 250-ml corner bottle containing 25 ml of a production medium, and then, shake-cultured at a speed of about 200 rpm at a temperature of 30° C. for 72 hours. After completion of the culture, the production of L-valine was measured by HPLC. The results of measuring the production of L-valine are shown in Table 4.

[Production Medium]

glucose 5%, ammonium sulfate 2%, monopotassium phosphate 0.1%, magnesium sulfate heptahydrate 0.05%, CSL 2.0%, biotin 200 μg/L, and pH 7.2

TABLE 4

| Production of valine in KCCM11201P | |
|---|---|
| Strain | Concentration of valine (g/L) |
| KCCM11201P | 2.8 |
| KCCM11201P/pECCG117-Pcj7-ilvE | 3.3 |
| KCCM11201P/pECCG117-Po2-ilvE | 3.7 |

As shown in the results of Table 4, it was confirmed that the Po2 resulted in improved production of valine in *Corynebacterium glutamicum* in which the expression of the ilvE gene was enhanced. In particular, the valine production in the strain named KCCM11201P/pECCG117-Po2-ilvE was significantly increased by about 32% compared to that in the control strain, and was increased by about 17% compared to that in the strain named KCCM10741P/pECCG117-Pcj7-ilvE. Consequently, it was confirmed that the Po2 influenced the enhanced expression of the ilvE gene.

[Accession Number]

Accession institution: Korean Culture Center of Microorganisms (international)

Accession number: KCCM11591P

Accession date: Oct. 23, 2014

According to the one or more of the exemplary embodiments above, a novel promoter may have various activities according to a microorganism used to induce expression of a target gene. In this regard, the novel promoter may be used in a case where activity of a target gene needs to be controlled during the production of the target product, resulting in efficient production of the target product.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described, it will be understood by those of ordinary skill in the art that various changes in form and details may be made therein without departing from the spirit and scope of the inventive concept as defined by the following claims.

The invention claimed is:

1. A synthetic promoter comprising the nucleotide sequence of SEQ ID NO: 1.

2. An expression regulatory sequence, comprising the promoter of claim 1.

3. A vector comprising the expression regulatory sequence of claim 2 and a target gene that is operatively linked to the expression regulatory sequence.

4. A host cell comprising the vector of claim 3.

5. The host cell according to claim 4, wherein the host cell is a bacterial cell belonging to the genus *Corynebacterium* or the genus *Escherichia*.

6. A method of producing a target product, the method comprising:

culturing the host cell of claim 4; and recovering the target product from the host cell or a culture medium including the cultured host cell.

7. The method of claim 6, wherein the target product is an amino acid.

8. A method of producing a target product, the method comprising:

culturing the host cell of claim 5; and recovering the target product from the host cell or a culture medium including the cultured host cell.

* * * * *

SEQUENCE LISTING

<160> NUMBER OF SEQ ID NOS: 18

<210> SEQ ID NO 1
<211> LENGTH: 86
<212> TYPE: DNA
<213> ORGANISM: Artificial Sequence
<220> FEATURE:
<223> OTHER INFORMATION: DNA sequence of O2 promoter

<400> SEQUENCE: 1
caataatcgt gaattttggc agcaacagaa ttatgtggta taatggaaac gtgcaaaagc 60
atagattatt ggaggagatc aaaaca 86

<210> SEQ ID NO 2
<211> LENGTH: 26
<212> TYPE: DNA
<213> ORGANISM: Artificial Sequence
<220> FEATURE:
<223> OTHER INFORMATION: forward primer for PCR of O2 promoter

<400> SEQUENCE: 2
ggtacccaat aatcgtgaat tttggc 26

<210> SEQ ID NO 3
<211> LENGTH: 26
<212> TYPE: DNA
<213> ORGANISM: Artificial Sequence
<220> FEATURE:
<223> OTHER INFORMATION: reverse primer for PCR of O2 promoter

<400> SEQUENCE: 3
gatatctgtt ttgatctcct ccaata 26

<210> SEQ ID NO 4
<211> LENGTH: 23
<212> TYPE: DNA
<213> ORGANISM: Artificial Sequence
<220> FEATURE:
<223> OTHER INFORMATION: forward primer for PCR of pGFPuv

<400> SEQUENCE: 4
gatatcatga gtaaaggaga aga 23

<210> SEQ ID NO 5
<211> LENGTH: 23
<212> TYPE: DNA
<213> ORGANISM: Artificial Sequence
<220> FEATURE:
<223> OTHER INFORMATION: reverse primer for PCR of pGFPuv

<400> SEQUENCE: 5
ctgcagttat ttgtagagct cat 23

<210> SEQ ID NO 6
<211> LENGTH: 729
<212> TYPE: DNA
<213> ORGANISM: Artificial Sequence
<220> FEATURE:
<223> OTHER INFORMATION: DNA sequence of GFP

<400> SEQUENCE: 6
gatatcatga gtaaaggaga agaacttttc actggagttg tcccaattct tgttgaatta 60
gatggtgatg ttaatgggca caaattttct gtcagtggag agggtgaagg tgatgcaaca 120
tacggaaaac ttacccttaa atttatttgc actactggaa aactacctgt tccatggcca 180

```
acacttgtca ctactttctc ttatggtgtt caatgctttt cccgttatcc ggatcatatg    240

aaacggcatg actttttcaa gagtgccatg cccgaaggtt atgtacagga acgcactata    300

tctttcaaag atgacgggaa ctacaagacg cgtgctgaag tcaagtttga aggtgatacc    360

cttgttaatc gtatcgagtt aaaaggtatt gattttaaag aagatggaaa cattctcgga    420

cacaaactcg agtacaacta taactcacac aatgtataca tcacggcaga caaacaaaag    480

aatggaatca aagctaactt caaaattcgc cacaacattg aagatggatc cgttcaacta    540

gcagaccatt atcaacaaaa tactccaatt ggcgatggcc ctgtcctttt accagacaac    600

cattacctgt cgacacaatc tgccctttcg aaagatccca acgaaaagcg tgaccacatg    660

gtccttcttg agtttgtaac tgctgctggg attacacatg gcatggatga gctctacaaa    720

taactgcag                                                            729
```

```
<210> SEQ ID NO 7
<211> LENGTH: 1167
<212> TYPE: DNA
<213> ORGANISM: Corynebacterium glutamicum

<400> SEQUENCE: 7

atggcagaaa aaggcattac cgcgccgaaa ggcttcgttg cttctgcaac gaccgcgggt     60

attaaagctt ctggcaatcc tgacatggcg ttggtggtta accagggtcc agagttttcc    120

gcagcggccg tgtttacacg taaccgagtt ttcgcagcgc ctgtgaaggt gagccgagag    180

aacgttgctg atggccagat cagggctgtt ttgtacaacg ctggtaatgc taatgcgtgt    240

aatggtctgc agggtgagaa ggatgctcgt gagtctgttt ctcatctagc tcaaaatttg    300

ggcttggagg attccgatat tggtgtgtgt tccactggtc ttattggtga gttgcttccg    360

atggataagc tcaatgcagg tattgatcag ctgaccgctg agggcgcttt gggtgacaat    420

ggtgcagctg ctgccaaggc gatcatgacc actgacacgg tggataagga aaccgtcgtg    480

tttgctgatg gttggactgt cggcggaatg ggcaagggcg tgggcatgat ggcgccgtct    540

cttgccacca tgctggtctg cttgaccact gatgcatccg ttactcagga aatggctcag    600

atcgcgctgg ctaatgctac ggccgttacg tttgacaccc tggatattga tggatcaacc    660

tccaccaatg acaccgtgtt cctgctggca tctggcgcta gcggaatcac cccaactcag    720

gatgaactca acgatgcggt gtacgcagct tgttctgata tcgcagcgaa gcttcaggct    780

gatgcagagg gtgtgaccaa gcgcgttgct gtgacagtgg tgggaaccac caacaacgag    840

caggcgatta atgcggctcg cactgttgct cgtgacaatt tgttcaagtg cgcaatgttt    900

ggatctgatc caaactgggg tcgcgtgttg gctgcagtcg gcatggctga tgctgatatg    960

gaaccagaga agatttctgt gttcttcaat ggtcaagcag tatgccttga ttccactggc   1020

gctcctggtg ctcgtgaggt ggatctttcc ggcgctgaca ttgatgtccg aattgatttg   1080

ggcaccagtg ggaaggcca ggcaacagtt cgaaccactg acctgagctt ctcctacgtg   1140

gagatcaact ccgcgtacag ctcttaa                                       1167
```

```
<210> SEQ ID NO 8
<211> LENGTH: 38
<212> TYPE: DNA
<213> ORGANISM: Artificial Sequence
<220> FEATURE:
<223> OTHER INFORMATION: forward primer for PCR of argJ

<400> SEQUENCE: 8
```

gagatcaaaa cagatatcat ggccaaaaaa ggcattac 38

<210> SEQ ID NO 9
<211> LENGTH: 36
<212> TYPE: DNA
<213> ORGANISM: Artificial Sequence
<220> FEATURE:
<223> OTHER INFORMATION: reverse primer for PCR of argJ

<400> SEQUENCE: 9
atcccccggg ctgcagttaa gagctgtacg cggagt 36

<210> SEQ ID NO 10
<211> LENGTH: 1104
<212> TYPE: DNA
<213> ORGANISM: Corynebacterium glutamicum

<400> SEQUENCE: 10
atgacgtcat tagagttcac agtaacccgt accgaaaatc cgacgtcacc cgatcgtctg 60
aaggaaattc ttgccgcacc gaagttcggt aagtacttca ccgaccacat ggtgaccatt 120
gactggaacg agtcggaagg ctggcacaac gcccaattag tgccatacgc gccgattcct 180
atggatcctg ccaccaccgt attccactac ggacaggcaa tttttgaggg aattaaggcc 240
taccgccatt cggacgaaac catcaagact ttccgtcctg atgaaaacgc cgagcgtatg 300
cagcgttcag cagctcgaat ggcaatgcca cagttgccaa ccgaggactt tattaaagca 360
cttgaactgc tggtagacgc ggatcaggat tgggttcctg agtacggcgg ggaagcttcc 420
ctctacctgc gcccattcat gatctccacc gaaattggct tgggtgtcag cccagctgat 480
gcctacaagt tcctggtcat cgcatcccca gtcggcgctt acttcaccgg tggaatcaag 540
cctgtttccg tctggctgag cgaagattac gtccgcgctg cacccggcgg aactggtgac 600
gccaaatttg ctggcaacta cgcggcttct ttgcttgccc agtcccaggc tgcggaaaag 660
ggctgtgacc aggtcgtatg gttggatgcc atcgagcaca agtacatcga agaaatgggt 720
ggcatgaacc ttgggttcat ctaccgcaac ggcgaccacg tcaagctagt cacccctgaa 780
ctttccggct cactacttcc aggcatcact cgcaagtcac ttctacaagt agcacgcgac 840
ttgggctacg aagtagaaga gcgaaagatc accaccaccg agtgggaaga agacgcaaag 900
tctggcgcca tgaccgaggc atttgcttgc ggtactgcag ctgttatcac ccctgttggc 960
accgtgaaat cagctcacgg caccttcgaa gtgaacaaca atgaagtcgg agaaatcacg 1020
atgaagcttc gtgaaaccct caccggaatt cagcaaggaa acgttgaaga ccaaaacgga 1080
tggctttacc cactggttgg ctaa 1104

<210> SEQ ID NO 11
<211> LENGTH: 36
<212> TYPE: DNA
<213> ORGANISM: Artificial Sequence
<220> FEATURE:
<223> OTHER INFORMATION: forward primer for PCR of ilvE

<400> SEQUENCE: 11
gagatcaaaa cagatatcat gacgtcatta gagttc 36

<210> SEQ ID NO 12
<211> LENGTH: 34
<212> TYPE: DNA
<213> ORGANISM: Artificial Sequence
<220> FEATURE:
<223> OTHER INFORMATION: reverse primer for PCR of ilvE

<400> SEQUENCE: 12
atcccccggg ctgcagttag ccaaccagtg ggta 34

<210> SEQ ID NO 13
<211> LENGTH: 26
<212> TYPE: DNA
<213> ORGANISM: Artificial Sequence
<220> FEATURE:
<223> OTHER INFORMATION: forward primer for PCR of aceP(WT)

<400> SEQUENCE: 13
ggtaccgtca ttacccccgc ctaacc 26

<210> SEQ ID NO 14
<211> LENGTH: 26
<212> TYPE: DNA
<213> ORGANISM: Artificial Sequence
<220> FEATURE:
<223> OTHER INFORMATION: reverse primer for PCR of aceP(WT)

<400> SEQUENCE: 14
gatatccaaa gtcacttcct taagtg 26

<210> SEQ ID NO 15
<211> LENGTH: 26
<212> TYPE: DNA
<213> ORGANISM: Artificial Sequence
<220> FEATURE:
<223> OTHER INFORMATION: forward primer for PCR of trcP

<400> SEQUENCE: 15
ggtaccctgc acggtgcacc aatgct 26

<210> SEQ ID NO 16
<211> LENGTH: 26
<212> TYPE: DNA
<213> ORGANISM: Artificial Sequence
<220> FEATURE:
<223> OTHER INFORMATION: reverse primer for PCR of trcP

<400> SEQUENCE: 16
gatatcctgt ttcctgtgtg aaattg 26

<210> SEQ ID NO 17
<211> LENGTH: 41
<212> TYPE: DNA
<213> ORGANISM: Artificial Sequence
<220> FEATURE:
<223> OTHER INFORMATION: forward primer for PCR of argJ

<400> SEQUENCE: 17
cgaaaggaaa cactcgatat catggccaaa aaaggcatta c 41

<210> SEQ ID NO 18
<211> LENGTH: 39
<212> TYPE: DNA
<213> ORGANISM: Artificial Sequence
<220> FEATURE:
<223> OTHER INFORMATION: forward primer for PCR of ilvE

<400> SEQUENCE: 18
cgaaaggaaa cactcgatat catgacgtca ttagagttc 39